(12) United States Patent
Duzy

(10) Patent No.: US 6,674,888 B1
(45) Date of Patent: Jan. 6, 2004

(54) TUNING METHOD FOR A PROCESSING MACHINE

(75) Inventor: Eyal Duzy, Nes-Ziona (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/032,117

(22) Filed: Feb. 27, 1998

(51) Int. Cl.[7] .................................................. G06K 9/00
(52) U.S. Cl. ...................................................... 382/148
(58) Field of Search ................................ 356/221, 392, 356/394; 382/145–149; 364/148

(56) References Cited

U.S. PATENT DOCUMENTS

| | | | | |
|---|---|---|---|---|
| 4,764,969 A | * | 8/1988 | Ohtombe et al. ............... 382/8 |
| 4,771,468 A | * | 9/1988 | Batchelder et al. ............ 382/8 |
| 5,383,018 A | * | 1/1995 | Sadjadi ....................... 356/243 |
| 5,394,322 A | * | 2/1995 | Hansen ....................... 364/148 |
| 5,495,535 A | * | 2/1996 | Smilansky et al. .......... 382/145 |
| 5,517,235 A | * | 5/1996 | Wasserman ................. 348/126 |
| 5,687,400 A | * | 11/1997 | Ishiguro et al. .............. 396/61 |
| 5,699,447 A | | 12/1997 | Alumot et al. .............. 382/145 |
| 5,761,336 A | * | 6/1998 | Xu et al. ..................... 382/141 |
| 5,764,793 A | * | 6/1998 | Omae et al. ................. 382/149 |
| 5,784,484 A | * | 7/1998 | Umezawa .................... 382/148 |
| 5,991,435 A | * | 11/1999 | Tsujikawa et al. .......... 382/147 |
| 6,014,455 A | * | 1/2000 | Sumiyoshi et al. ......... 382/144 |
| 6,064,484 A | * | 5/2000 | Kobayashi et al. ......... 356/390 |
| 6,115,491 A | * | 9/2000 | Rudd et al. ................. 382/154 |

* cited by examiner

*Primary Examiner*—Quyen Leung
*Assistant Examiner*—Davienne Monbleau
(74) *Attorney, Agent, or Firm*—Sughrue Mion LLP.

(57) ABSTRACT

A method for setting at least one selected parameter of a processing tool. The processing tool is utilized for processing articles in a production line. Initially, the selected parameter is set to an initial value and one such article is positioned for processing. The article is sequentially processed by the processing tool a certain number of times and corresponding processed data are obtained. The processed data are analyzed so as to determine whether or not the processed data satisfy predetermined result criteria. Upon detecting that the processed data do not satisfy the result criteria, the selected parameter is changed to a tuned value and the processing, obtaining the processed data and analyzing thereof, are repeated as many times as required until the result criteria is satisfied.

18 Claims, 3 Drawing Sheets

TUNING METHOD FOR A PROCESSING MACHINE

FIELD OF THE INVENTION

The present invention is in the field of tuning techniques and relates to a method for setting the parameters of a machine tool used for processing articles, such as optical inspection or metrology tool.

BACKGROUND OF THE INVENTION

There is a great variety of manufacturing and technological processes whose success depend significantly on correct tuning of the parameters of a processing machine prior to its operation. The problem becomes more essential when the process contains several operational procedures requiring different values of the machine's parameters to be set.

For example, manufacturing of semiconductor wafers is a very complicated process consisting of forming grid-like multi-layered structures, wherein several non-destructive post-process optical inspections should be carried out after different manufacturing stages. It is known that different manufacturing stages require different levels of inspection sensitivity. Inspection sensitivity prescribes, for example, a threshold according to which an inspected location is reported as fault-free or defective. Thus, for example, a post Chemical Mechanical Planarization (CMP) inspection phase typically aimed at identifying micro-scratches imposes different inspection sensitivity than that of a post etching phase aimed at pattern defects and particle identification. Incorrect inspection sensitivity, either overstated or understated, leads to undesirable results. For example, either fault-free wafers are identified as defective (due to overstated inspection sensitivity) and are, therefore, removed from the production line or really defective wafers are classified as fault free (due to understated inspection sensitivity) and therefore proceed to next production stages.

A tuning phase conventionally applied in order to reach the desired sensitivity level, typically (although not necessarily) includes the following steps. An inspection tool, which may occupy a certain working station of a production line, is set for a given inspection sensitivity level and a wafer is inspected, resulting in the provision of a list of detected locations referred to as a defect map. Then, the inspected wafer is moved from the inspection tool to a verification tool that may be accommodated within the same working station, or alternatively constitutes a stand-alone tool. The verification tool typically comprises an optical or scanning electron microscope (SEM) and utilizes high resolution imaging for verifying whether the so reported defected locations are indeed defective, or otherwise fault-free. If it is determined (after tuning, inspection and review cycle) that the number of faulty defects is too high, the wafer is returned to the inspection tool and the specified tuning, inspection-and-review cycle is repeated until the desired level of sensitivity is substantially achieved.

One example of the conventional tuning phase of the wafers inspection apparatus is disclosed in U.S. Pat. No. 5,699,447 and is schematically illustrated in FIG. 1. The apparatus, generally designated 1 includes a table 2 for receiving the wafer W to be inspected and two examining systems, generally at $PH_1$ and $PH_2$, for performing so-called "Phase I" and "Phase II" examinations, respectively, of the same wafer. To this end, as illustrated in a self-explanatory manner, table 2 is controlled by a movement control system (not shown) to effect the proper positioning of the wafer W on the table in each of the Phase I and Phase II examination phases. The system $PH_1$ inspects the wafer W and detects suspected locations thereon having a high probability of a defect. For this purpose, a plurality of detectors 5 detect light scattered from the wafer W and transmit data representative thereof to an image processor 7, whose operation is based on a so-called "Decision Table", which makes a decision as to whether a logical output indicating the existence of a defect at a given location should be issued or not. Information indicative of these locations is stored within a storage device in a main controller 8. Only the suspected locations having a high probability of a defect are examined by the system $PH_2$. The system $PH_2$ carries out relatively high resolution and low speed inspection, relative to that of the system $PH_1$ by imaging the suspected location on an opto-electric converter 9, whose output is connected to an image processor 11, which, under the control of the main controller 8, outputs information indicating the presence or absence of a defeat in each inspected location examined during Phase I. It is appreciated that Phases I and II are sequentially repeated, until the inspection sensitivity of the system $PH_1$ reaches the correct value.

Such a conventional tuning-inspection-review phase is not only burdensome, but also time consuming, and may extend over 2–3 hours or more. If articles, which are to be inspected, progress on a production line, the production process has to be halted until the completion of the tuning phase. It should be noted that during the entire tuning-inspection-review phase the inspection and review tools may be utilized solely to this end. Put differently, during the entire period that the article undergoes review in the review tool, the inspection tool should remain in a standby mode incapable of being used in other manufacturing tasks. This disadvantage is of particular relevance when stand-alone inspection and review tools are employed. Moreover, insofar as stand-alone tools are concerned, transmitting of the article to and from the inspection and review tools results in additional loading-unloading and, consequently, known per se time consuming and error-prone handling procedures.

SUMMARY OF THE INVENTION

There is accordingly need in the art to substantially reduce or overcome the specified disadvantages by a novel method for tuning a processing machine suitable for the conditions of a specific process.

It should be noted that for convenience of explanation only the description refers by way of example only to tuning of inspection tools that inspect wafers. The invention is by no means bound to this specific example.

There is provided according to the present invention a method for setting at least one selected parameter of a processing tool that is utilized for processing articles in a production line, comprising:

a) setting said at least one selected parameter to an initial value;

b) processing an article by the processing machine and obtaining processed data indicative of features of the article, wherein said processing and obtaining the processed data are repeated a certain number of times;

c) analyzing the so obtained processed data so as to determine whether or not the processed data satisfy a predetermined result criteria;

d) upon detecting that the processed data do not satisfy the result criteria, tuning said at least one selected parameter to a tuned value; and e) applying said steps (b), (c) and (d) as many times as required until said result criteria is essentially satisfied.

The underlying idea of the invention is to exploit the fact that inspection of articles, especially semiconductor wafers, has a statistic nature. Accordingly, several inspection procedures applied to same article, normally give rise to different inspection results. In this specific case of an optical inspection in order to locate defects, successive inspection runs provide different lists of possible defects. To this end, a certain results criteria is set, in order to determine a desired sensitivity level. Thus, for example, the result criteria may prescribe an acceptable tolerance between the inspection results obtained by a certain number of inspection procedures.

It is appreciated that the processing machine may be of any kind capable of performing inspection of articles, such as optical inspection, metrology, etc. Such a machine typically comprises illuminator and detector units and suitable light directing optics. By way of one non limiting example, the parameters which are to be set may include any one or a combination of the power of a light source used in the illuminator unit, the sensitivity of the detector unit, the autofocusing factor of the directing optics, etc. Additionally, the selected parameters may include a decision table defining the processing results. Other parameters may be used in lieu or in addition to the specified parameters, all as required and appropriate, depending upon the particular application.

It is thus evident that numerous burdensome and time-consuming steps of a conventional tuning phase are advantageously replaced here by the several steps of a certain, quickly executable model. The latter does not require the provision of any additional equipment and significantly speeds up the tuning phase.

More specifically, the present invention is used for post-process automatic optical inspection of articles progressing on a production line and is therefore described below with respect to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

In order to more clearly illustrate the unique features of the present invention, it would be reasonable to more specifically consider the main principles of a conventional approach for tuning a processing machine, for example, for automatic optical inspection of articles progressing on a production line. The construction and operation of such machine is known per se and therefore need not be specifically described except to note that it typically includes illumination and detector units, appropriate optical system and a processor coupled to the detector unit.

Figure 1:
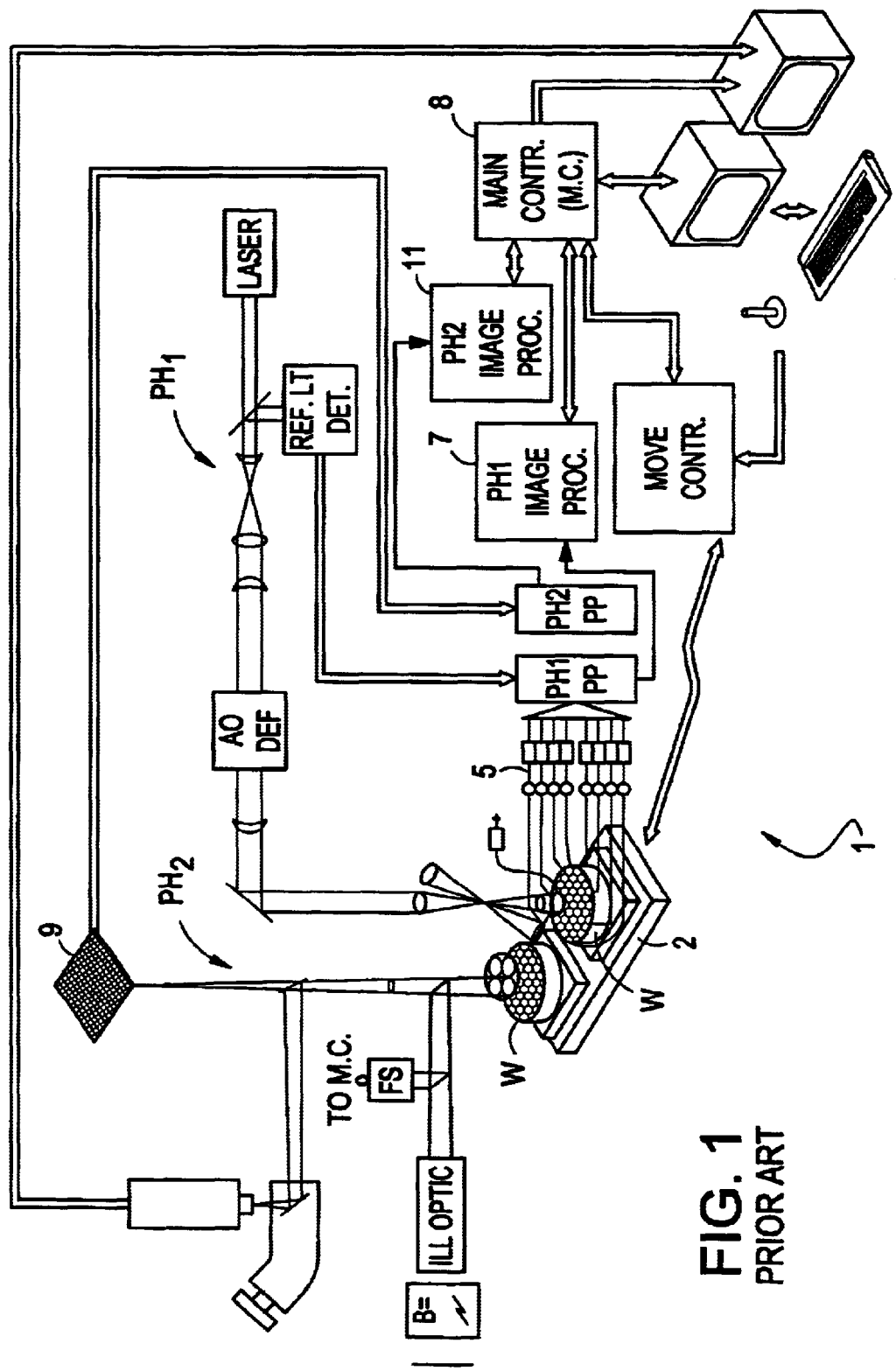
FIG. 1 is a schematic illustration of the main components of a conventional inspection apparatus implementing a tuning phase.
Figure 2:
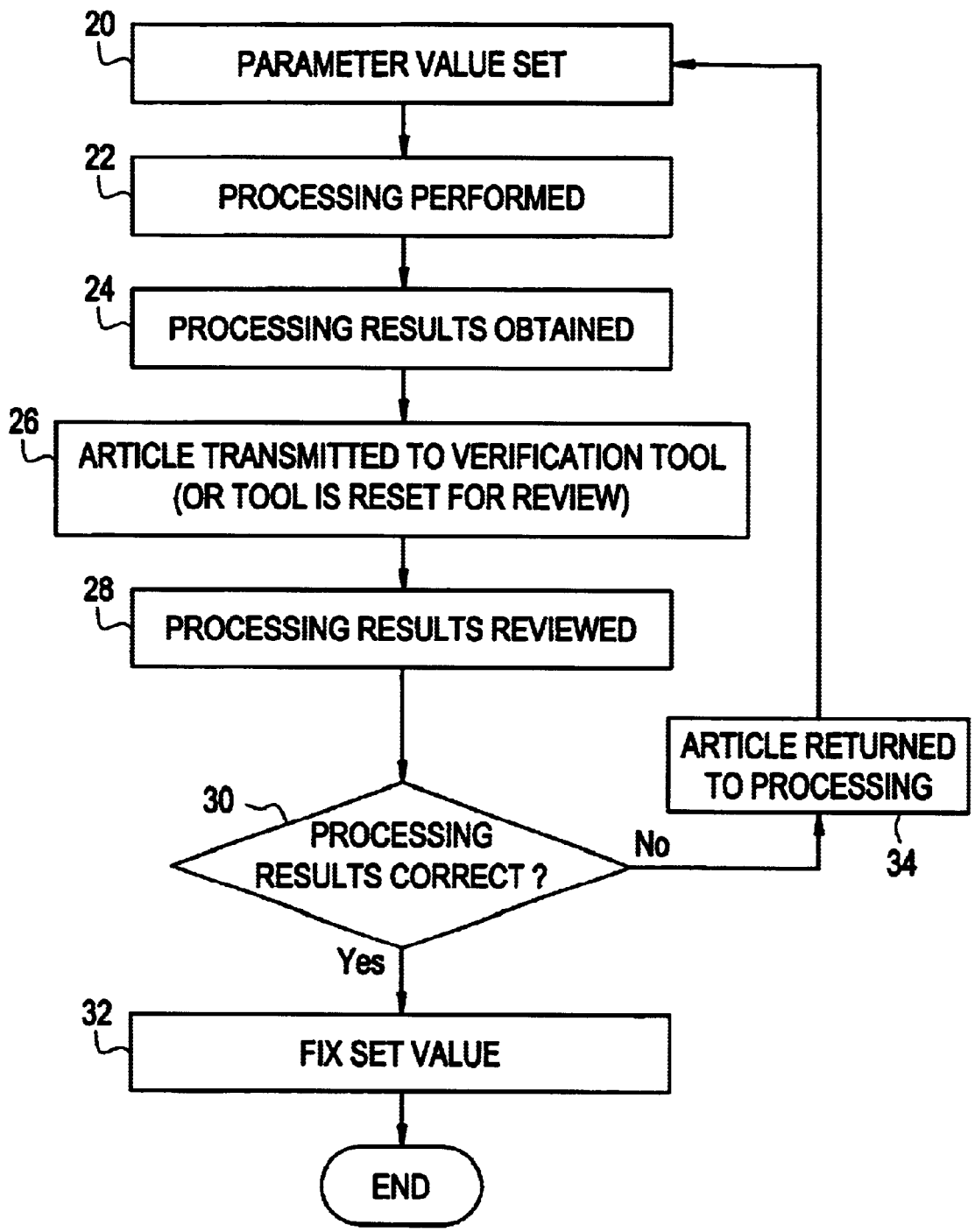
FIG. 2 is a flow diagram of the main steps according to the conventional tuning phase.

FIG. 2 illustrates the main steps of the conventional procedure for tuning the inspection sensitivity. Initially, the detector sensitivity is set to a certain initial value (step 20) and the automatic optical inspection of the article is performed (step 22) resulting in obtaining the list of possible defects (step 24). Then, the article is transmitted from the inspection tool to a verification tool (step 26). The construction and operation of the verification tool are also known per se, employing high resolution, low speed optical system, for example, such as that disclosed in the above U.S. Pat. No. 5,699,447. It is appreciated, although not specifically shown, that additional loading/unloading or conveying means are provided for this purpose. The results of the automatic inspection are now reviewed (step 28) so as to detect whether or not they are correct (step 30). If it appears that the inspection results are correct, the initial value of the detector sensitivity is fixed (step 32), the tuning phase is completed and the automatic inspection of the progressing articles starts. If the results are incorrect, e.g. too much faulty defects are detected, the article is retuned to the inspection machine (step 34), the detector sensitivity is changed accordingly and the tuning phase is repeated starting from step (20).

Figure 3:
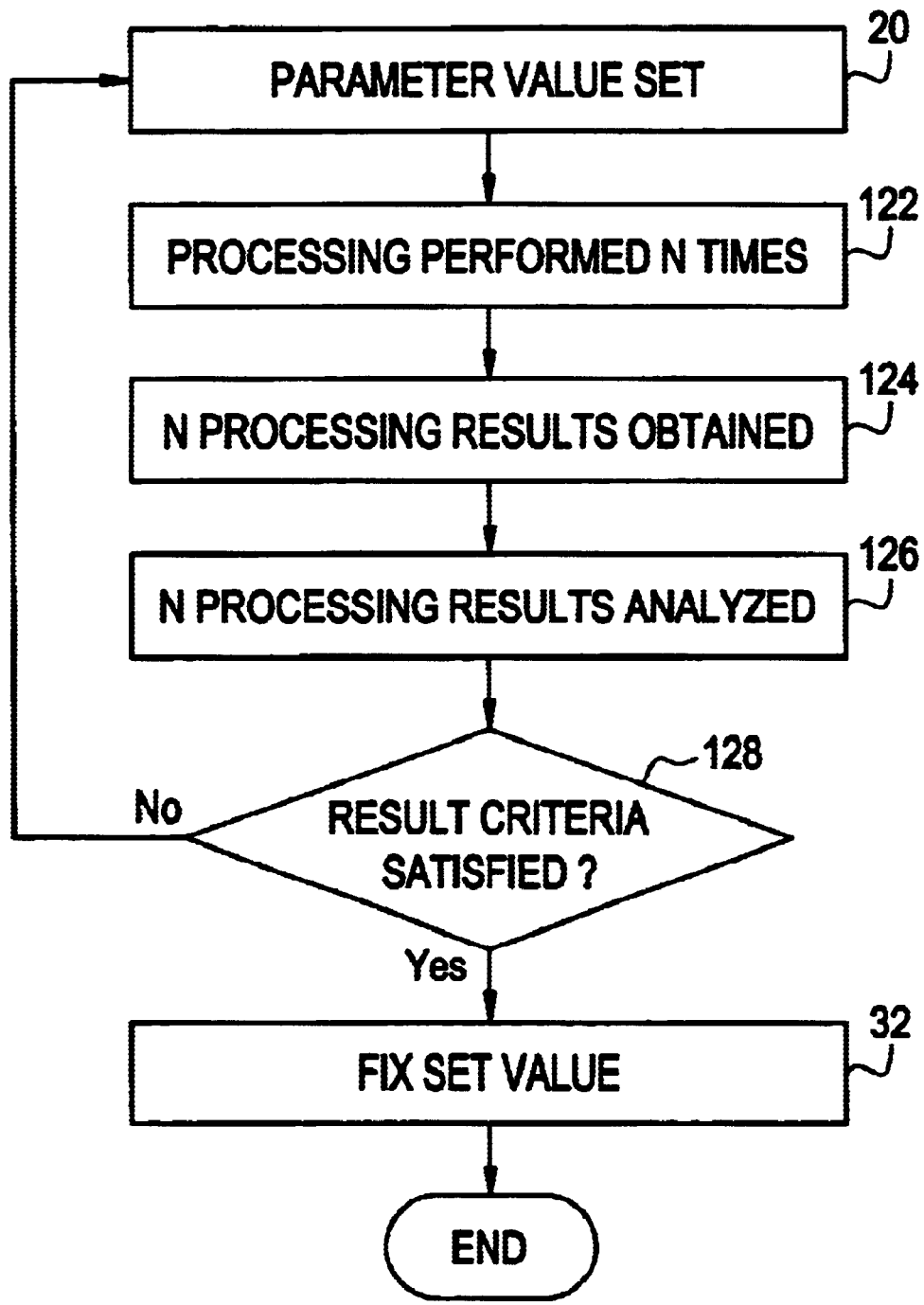
FIG. 3 is a flow diagram illustrating the main principles of a tuning method according to the invention.

Reference is now made to FIG. 3, illustrating the main principles of a tuning method according to the present invention. The same reference numbers are used for identifying those steps, which are common in the conventional and invented methods. In order to facilitate understanding, assume that the tuning method is to be applied to a processing machine of the same kind and, similarly, the detector sensitivity is to be tuned.

One of the essential features of the present invention consists in that, in distinction to the conventional approach, there is no need for a verification tool or any other equipment in addition to that included in the production line, except for the optional provision of additional software applied in the inspection tool processor, the purpose of which will be described further below.

Thus, according to a certain manufacturing process, an article to be optically inspected arrives to a processing station occupied by the inspection tool. The article is located in its ready-to-inspect position and an initial value of the detector sensitivity is set (step 20).

According to another essential feature of the preferred embodiment, the automatic optical inspection is sequentially performed a certain number N of times (step 122) and corresponding results indicative of possible defects in the article are obtained. Immediately thereafter the processing results are analyzed (step 126) so as to detect whether or not they satisfy a predetermined results criteria (step 128). It should be specifically noted that results may be analyzed by an operator, in which case they are displayed on a monitor (not shown) coupled to the processor unit, or by the additional software. The results criteria are in the form of a preset range defining an acceptable tolerance between the N inspection results. The inspection results are compared to each other and if the differences are within the accepted tolerance, the initially set value of the detector sensitivity is fixed (step 32) being considered a correct one and the automatic inspection of the progressing articles continues. If not, the parameter is changed and the tuning procedure is repeated again.

For example, the article is scanned ten times, each time detecting several defects. For each detected defect, it is analyzed in how many scans it appears. Assume that a threshold (constituting the "Decision Table") is equal to seven. Then, if a specific detected defect appears in seven of the ten scans, it is considered to be a real defect and if not, it is a false defect. If the number of so obtained false defects is too great, the initial sensitivity is too high and vice versa.

It is appreciated that the processing phase, which is an optical inspection in the present example, may be repeated as many times as desired. Similarly, the threshold, defining, processed data, and result criteria of the tuning phase may vary in accordance with the specific application.

It will be readily understood that the above method is substantially fast, in comparison to the conventional one since it does not require the slower review step at each tuning step.

It should be noted, although not specifically shown, that the method described above may optionally include the review step for verifying the obtained conclusions or for increasing the level of confidence. For example, this review step may be performed only at the last setting aiming at sampling some of the finding resulting from the analysis using the multiple automatic inspections by means of the inspection tool. That is, one may use the inventive method to quickly arrive at an adequate setting, and then use the review to verify that the setting is an optimum setting.

It should also be noted that in the above description, the review step can be done using the inspection tool itself, by, for example, changing the magnification and using the defect map to look at the defect locations using higher magnification. That is, one may use low magnification to perform a fast scan of the substrate (semiconductor wafer, reticle, or mask) and obtain a defect mat of suspected locations. Then the objective can be changed to obtain a higher magnification and a slow review of the suspected location designated in the defect map can be performed.

Those skilled in the art will readily appreciate that many modifications and changes may be applied to the invention as hereinbefore exemplified without departing from its scope defined in and by the appended claims. In the method claims that follow claim steps, are provided for convenience only and do not apply any particular order of performing the steps.

What is claimed is:

1. A method for setting at least one selected parameter of a processing tool that is utilized for processing articles in a production line, comprising:
    a) determining an initial value for said at least one selected parameter;
    b) processing an article by the processing tool and generating processed data indicative of features of the article, wherein said processing of the article and said generating of the processed data are repeated at a same resolution for a predetermined number of times;
    c) analyzing the processed data for the article by comparing each of the predetermined number of generated processed data to one another in order to determine how many of the predetermined number of generated processed data contain a same features, so as to determine whether or not the processed data satisfy a predetermined result criteria;
    d) upon determining that the processed data do not satisfy the result criteria, tuning said at least one selected parameter to a tuned value; and
    e) applying said steps (b), (c) and (d) as many times as required until said result criteria is satisfied.

2. The method according to claim 1, wherein said analyzing comprises the steps of:
    checking the frequency of appearance of each of said features on the basis of each of said processed data.

3. The method according to claim 1, wherein said predetermined result criteria is in the form of a threshold defining a frequency of appearance of each of said features in processed data during said predetermined number of times.

4. The method according to claim 1, wherein said processing tool is a first processing tool and wherein the method also comprises the step of:
    reviewing the article by another processing tool that is different from said first processing tool, upon detecting that the processed data do not satisfy the result criteria.

5. The method according to claim 1, wherein the processing tool is adapted for inspection of the articles.

6. The method according to claim 1, wherein said processing tool is adapted for optical inspection of the articles, the tool including illumination and detector units and a light directing optics.

7. The method according to claim 2, wherein said inspection is operative to locate and classify defects on the article.

8. The method according to claim 2, wherein said inspection includes a metrology procedure for measuring parameters of the articles.

9. The method according to claim 1, wherein the article to be processed is a semiconductor wafer.

10. The method according to claim 1, wherein the article to be processed is a reticle.

11. The method according to claim 1, wherein the article to be processed is in the form of a patterned structure.

12. The method according to claim 3, wherein said at least one selected parameter is a power of the illumination unit.

13. The method according to claim 3, wherein said at least one selected parameter is a sensitivity of the detector unit.

14. The method according to claim 3, wherein said at least one selected parameter comprises a factor indicating the autofocusing of the light directing optics.

15. The method according to claim 1, wherein said at least one selected parameter comprises the content of a decision table defining a threshold level for obtaining the processed data.

16. The method according to claim 1 wherein said processing tool is set to a first sensitivity value, further comprising the step of:
    reviewing the article by said processing tool using a second sensitivity value, upon detecting that the processed data do not satisfy the result criteria.

17. The method according to claim 16 wherein said first sensitivity value is greater than said second sensitivity value.

18. The method according to claim 16 where said first sensitivity value is representative of a low magnification-to-surface fast scan movement and said second sensitivity is representative of a high magnification-to-surface slow scan movement.

* * * * *